United States Patent [19]

Stark, Jr.

[11] 4,288,603
[45] Sep. 8, 1981

[54] SILYLATED CATECHOL COMPOSITIONS

[75] Inventor: Charles J. Stark, Jr., Clifton Park, N.Y.

[73] Assignee: General Electric Company, Schenectady, N.Y.

[21] Appl. No.: 168,036

[22] Filed: Jul. 14, 1980

[51] Int. Cl.³ .......................... C07F 7/08; C07F 7/10; C07F 7/18
[52] U.S. Cl. .................................. 556/422; 556/486; 556/443
[58] Field of Search .................. 556/422, 443, 486

[56] References Cited

U.S. PATENT DOCUMENTS 2,962,410 11/1960 Kohn et al. .......................... 154/140
3,137,720 6/1964 Cooper ........................... 556/443 X
3,328,450 6/1967 Plueddemann ...................... 556/443
3,489,783 1/1970 Shepard et al. ................ 556/486 X
3,546,267 12/1970 Ismail .............................. 556/486 X
3,576,032 4/1971 Pearce .................................. 556/443
3,812,214 5/1974 Markovitz .................. 260/830 TW

FOREIGN PATENT DOCUMENTS 879572 10/1961 United Kingdom ................ 556/443

Primary Examiner—Paul F. Shaver
Attorney, Agent, or Firm—Joseph T. Cohen; James C. Davis, Jr.

[57] ABSTRACT

Accelerators useful for the cure of epoxy resin compositions are derived from the silylation of substituted catechol derivatives.

8 Claims, No Drawings

SILYLATED CATECHOL COMPOSITIONS

This invention is concerned with novel compositions useful as accelerators for thermally curable epoxy resins, such as those disclosed in my copending application, Ser. No. 168,037, filed July 14, 1980 and assigned to the same assignee as the present invention, and incorporated herein by reference. More particularly, the accelerator compositions (hereinafter referred to as "accelerators") of the present inventions are derived from the silylation of catechol derivatives having the aryl group substituted with select radicals, and have the following general formula:

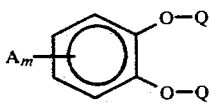   I.

where Q is independently selected from the class consisting of Si—$R_3$ or hydrogen, R is independently selected from the class consisting of hydrogen, monovalent alkyl (including aralkyl) groups of from 1 to 8 carbon atoms (e.g. methyl, ethyl, benzyl, propyl, isopropyl, hexyl, etc.), aryl (e.g. phenyl, naphthyl, etc.), alkaryl (e.g., tolyl, etc.), vinyl and allyl radicals; A is independently selected from alkyl radicals the same as R above, halogen (e.g., chlorine, bromine, etc.) and the nitro radical, where A can be ortho-, meta-, or para- to either of the -OQ radicals and m is an integer from 1 to 2, inclusive, with the proviso, that only one Q can be hydrogen, and only one R can be hydrogen on any silicon atom.

The cure accelerators corresponding to formula I, may be prepared by reacting, in the presence of an inert solvent, such as toluene or benzene, a catechol of the formula

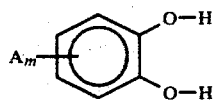   II.

with a halogenosilane of the formula

   III.

where X is a halogen radical, e.g. chlorine, bromine, etc, and where R, A, and m have the meanings above. In addition, a hydrohalide acceptor, such as pyridine, triethylamine, etc. may be used to effect the above reaction.

The determination whether 1 or 2 of the OQ radicals in formula I will be $SiR_3$ groupings will depend on the molar concentrations of the ingredients. For instance, if one desires to have only one —$OSiR_3$ and one OH group on the catechol derivative of formula I, one will normally employ 1 mol of the organohalogenosilane of formula III per mole of the catechol derivative of formula II. Where, however, it is desired to have two —$OSiR_3$ groupings attached directly to the aromatic nucleus of the catechol derivative of formula I, one will normally employ 2 mols of the organohalogenosilane of formula III per mole of the catechol derivative of formula II. Slight molar excesses of the organohalogenosilane of formula III may be employed as long as the formation of the desired catechol derivative of formula I is not jeopardized. The examples described in the instant application will exemplify the molar relationships of ingredients required to make the catechol derivatives of formula I.

Generally, the compounds corresponding to formula I are prepared by effecting reaction between the organohalogenosilane of formula III with the catechol derivative of formula II in the presence of the hydrohalide acceptor. It will of course be understood that under some conditions the hydrohalide acceptor may be omitted where the rate of reaction between the reactants produces the desired compound coming under formula I without the need of the hydrohalide acceptor. Normally, the halosilane is added to a solution of the catechol derivative of formula II, the hydrohalide acceptor and an inert solvent, such as toluene, benzene, diethyl ether, etc., after which the catechol solution is heated under reflux conditions. Thereafter, the formed amine hydrohalide (if an amine is used as the hydrohalide acceptor) is removed by filtration and the remainder of the reaction mixture neutralized, and then subjected to fractional distillation to isolate the desired catechol derivatives of formula I.

It will of course be apparent to those skilled in the art that because difficulty may be encountered in isolating pure compounds of formula I, there may be slight contamination of the desired compound; however, if any contaminants are present, they will be in such small amounts as to have no adverse effect on the use of the compositions of formula I for the intended purpose of accelerating the cure of epoxy resins. The method of determining the chemical composition of the catechol derivatives of formula I generally comprised using NMR or similar analytical methods.

Examples of the halogenosilanes which may be used in the preparation of the novel accelerators of the instant invention include, e.g., trimethylchlorosilane, allyldimethylchlorosilane, benzyldimethylchlorosilane, t-butyldimethylchlorosilane, methyldiethylchlorosilane, chloropropyldimethylchlorosilane, phenyldimethylchlorosilane, diethylchlorosilane, dimethylchlorosilane, diphenylchlorosilane, diphenylvinylchlorosilane, methylethylchlorosilane, n-octyldimethylchlorosilane, vinyldimethylbromosilane, etc.

The novel compositions of the present invention have particular application as accelerators for curing a variety of epoxy resin compositions which include any 1,2-epoxy resin having more than 1 epoxy group per molecule; many such epoxy resins are disclosed in my copending application mentioned above, Serial Number 168,037 (RD-12,665) filed July 14, 1980, and which by reference is incorporated in the instant application. Other epoxy resins well known in the art set forth, for example, in many patents including U.S. Pat. Nos. 2,324,483, 2,444,333, 2,494,295, 2,500,600 and 2,511,913.

In order that those skilled in the art will be better able to practice the invention, the following examples are given by way of illustration and not by way of limitation. All parts are by weight unless otherwise indicated.

EXAMPLE 1

A solution of 30 grams 4-t-butylcatechol and 60.3 grams triethylamine, dissolved in 75 ml. toluene, was added 42 grams trimethylchlorosilane dissolved in 20 ml. toluene. The resultant mixture was allowed to reflux for twelve hours, then allowed to cool. After filtration of the insoluble aminehydrochloride, the volatiles were removed by flash evaporation. The residue was dissolved in toluene and pentane, then washed with cold water, and saturated with an aqueous sodium bicarbonate solution. The organic layer was then isolated, dried with magnesium sulfate, and condensed by flash evaporation. Distillation at 1.75 Torr produced a compound corresponding to the formula

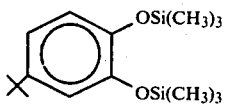
IV.

The identity of this compound was established by NMR.

EXAMPLE 2

To 10 grams 4-nitrocatechol, dissolved in 25 ml. diethylether was added 25.0 grams trimethylchlorosilane dissolved in 25 mol. diethylether. The mixture was refluxed for twelve hours, then cooled and filtered. Removal of volatiles by flash evaporation, followed by distillation of the residue at 1.75 Torr yielded a composition of the formula

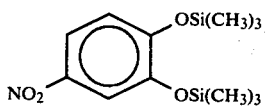
V.

EXAMPLE 3

30 Grams 4-t-butylcatechol, 19.6 grams trimethylchlorosilane and 100 ml. toluene were mixed and heated at the reflux temperature of the mass for twelve hours. After this time, the mixture was condensed and distilled under vacuum. The accelerator obtained corresponded to the formula

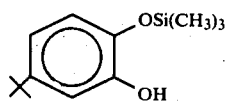
VI.

EXAMPLE 4

A solution composed of 19.2 triethylamine, 50 ml. toluene and 30 grams 4-t-butylcatechol was heated to reflux temperature at which point 22.1 grams dibutyl-t-butylchlorosilane dissolved in 50 ml. of toluene, was added dropwise. After refluxing for 12 hours, the reaction mixture was cooled and filtered to remove the amine hydrochloride. The filtrate was condensed by flash evaporation and then distilled at 0.75 Torr to yield a composition corresponding to the formula

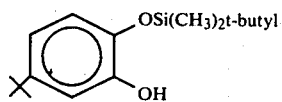
VII.

EXAMPLE 5

A solution consisting of 30 grams 4-chloro-catechol, 55 grams triethylamine, and 50 ml. toluene and 47.3 parts trimethylchlorosilane is heated at reflux for 12 hours. The mixture is cooled and the solids filtered off. The volatiles are removed by flash evaporation and the resulting residue is distilled at reduced pressure to yield an accelerator composition of the formula

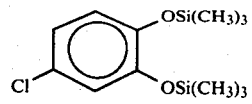
VIII.

EXAMPLE 6

A solution of 30 grams 4-chlorocatechol, 41 grams dimethylchlorosilane, and 150 ml. toluene are heated to reflux under a blanket of nitrogen. After the reaction is adjudged complete by vapor phase chromatography, the material is cooled and the volatiles removed by flash evaporation. The residue is then distilled at reduced pressure to yield a composition corresponding to the formula

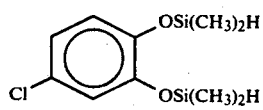
IX.

EXAMPLE 7

To a refluxing solution of 30 grams 4-methylcatechol dissolved in 150 ml. toluene and 55 grams triethylamine is added 87 grams dimethylphenylchlorosilane dissolved in 50 ml. toluene. After 12 hours, the reaction mixture is allowed to cool and the amine hydrochloride is filtered off. Toluene, unreacted chlorosilane and triethylamine are removed by flash evaporation. Distillation of the residue yields a compound corresponding to the formula

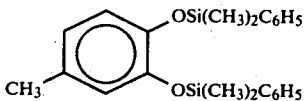
X.

Although the above examples are directed to only a few of the very many variables of the formulations representing the novel accelerators of the present invention, it should be understood that the novel accelerators according to the present invention can comprise a much broader variety and mixture of compositions, the positions of the substituents on the aryl nucleus can be varied as shown in the description and general formula preceding these examples. In addition, it should be noted that the identity of compounds I-X were established by NMR.

What I claim as new and desire to secure by Letters Patent of the United States is:

1. A composition of matter having the general formula where Q is independently selected from the class consisting of Si—R$_3$ or hydrogen and, R is independently selected from the class carbon atoms, aryl, alkaryl, aralkyl, vinyl, and allyl radicals, A is independently selected from alkyl radicals the same as R above, halogen and the nitro radical, where A can be ortho-, meta or para- to either of the —OQ radicals, and m is an integer from 1 to 2 inclusive, with the proviso, that only one Q can be hydrogen, and only one R can be hydrogen on any one silicon atom.

2. A composition of matter of the formula

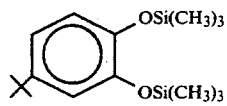

3. A composition of matter of the formula

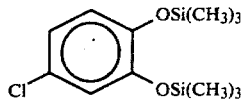

4. A composition of matter of the formula

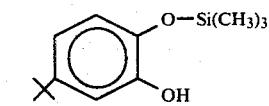

5. A composition of matter of the formula

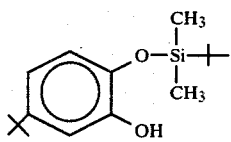

6. A composition of matter of the formula

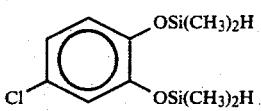

7. A composition of matter of the formula

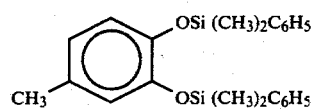

8. A composition of matter of the formula

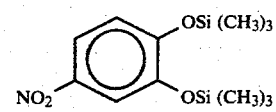

* * * * *